(12) United States Patent
Shimizu et al.

(10) Patent No.: US 7,677,727 B2
(45) Date of Patent: Mar. 16, 2010

(54) EYE REFRACTIVE POWER MEASUREMENT APPARATUS

(75) Inventors: Kazunari Shimizu, Gamagori (JP); Kenji Nakamura, Toyohashi (JP)

(73) Assignee: Nidek, Co., Ltd., Gamagori-shi (JP)

( * ) Notice: Subject to any disclaimer, the term of this patent is extended or adjusted under 35 U.S.C. 154(b) by 0 days.

(21) Appl. No.: 12/230,603

(22) Filed: Sep. 2, 2008

(65) Prior Publication Data

US 2009/0059169 A1   Mar. 5, 2009

(30) Foreign Application Priority Data

Sep. 3, 2007   (JP)   ............................. 2007-228344
Jul. 22, 2008   (JP)   ............................. 2008-188545

(51) Int. Cl.
*A61B 3/10*   (2006.01)

(52) U.S. Cl. ..................... 351/205; 351/206; 351/212

(58) Field of Classification Search ................. 351/205, 351/206, 210, 211, 212, 214, 221
See application file for complete search history.

(56) References Cited

U.S. PATENT DOCUMENTS 5,886,780 A   3/1999   Fukuma et al.

2005/0157261 A1   7/2005   Hanebuchi et al.
2005/0270488 A1*   12/2005   Hanebuchi .................. 351/214
2007/0070293 A1*   3/2007   Isogai ......................... 351/205

FOREIGN PATENT DOCUMENTS

| JP | A-01-129830 | 5/1989 |
| JP | A-09-276221 | 10/1997 |
| JP | B2-3071693 | 5/2000 |
| JP | A-2005-185523 | 7/2005 |
| JP | A-2007-089715 | 4/2007 |

* cited by examiner

*Primary Examiner*—Huy K Mai
(74) *Attorney, Agent, or Firm*—Oliff & Berridge, PLC

(57) ABSTRACT

An eye refractive power measurement apparatus capable of performing analysis of an examinee's eye for irregular astigmatism with accuracy comprises a measurement optical system comprising an optical system projecting measurement light onto an examinee's fundus and an optical system photo-receiving the measurement light as a ring or substantially-ring fundus reflection image, a light deflection member placed in the optical systems, a unit rotating the deflection member, a memory storing the photo-received image as a measurement image, an analysis unit performing analysis of the measurement image, and an output unit, wherein the analysis unit detects the number of images or a width of an image in each meridian direction in the measurement image and judges the eye has irregular astigmatism when a portion in which the number of the images is two or a portion in which the width of the image goes beyond a predetermined level is detected.

7 Claims, 6 Drawing Sheets

EYE REFRACTIVE POWER MEASUREMENT APPARATUS

BACKGROUND OF THE INVENTION

1. Field of the Invention

The present invention relates to an eye refractive power measurement apparatus which measures refractive power of an examinee's eye objectively.

2. Description of Related Art

Conventionally, there is known an eye refractive power measurement apparatus comprising a projection optical system for projecting a measurement target onto a fundus of an examinee's eye and a photo-receiving optical system in which a ring-shaped opening is placed in a position conjugate with a pupil of the eye, for photo-receiving reflection light from the fundus as a ring fundus reflection image on a two-dimensional image-pickup element, the apparatus arranged to perform measurement of refractive power of the eye based on a photo-received position of the ring image which is picked up by the two-dimensional image-pickup element.

In addition, an eye refractive power measurement apparatus is disclosed, which has a configuration as described above and is further arranged to display on a monitor a standard deviation as irregular astigmatic power, the standard deviation obtained from differences between refractive power in meridian directions of the eye which is obtained from a ring fundus reflection image subjected to ellipse fitting in order to obtain sphere power, astigmatic power and an astigmatic axial angle of the eye, and refractive power in the meridian directions of the eye which is obtained from an actual fundus reflection image (see Japanese Patent Application Unexamined Publication No. Hei09-276221).

However, when refractive power measurement of an eye of an examinee who has keratoconus that is a kind of irregular astigmatism and analysis of the eye for irregular astigmatism are performed, there is a case where a ring image picked up by the two-dimensional image-pickup element does not greatly differ from that of an examinee's eye which has regular astigmatism. In this case, the eye of the examinee who has keratoconus could be interpreted as a normal eye.

SUMMARY OF THE INVENTION

An object of the invention is to overcome the problems described above and to provide an eye refractive power measurement apparatus capable of performing analysis of an examinee's eye for irregular a stigmatism with accuracy.

To achieve the objects and in accordance with the purpose of the present invention, an eye refractive power measurement apparatus comprises a measurement optical system comprising a projection optical system for projecting measurement light onto a fundus of an examinee's eye and a photo-receiving optical system having a two-dimensional image-pickup element for photo-receiving the measurement light reflected from the fundus on the image-pickup element as a ring fundus reflection image or a substantially-ring fundus reflection image which is formed by a plurality of spot fundus reflection images, a light deflection member which is placed in the projection optical system and the photo-receiving optical system and is positioned aside from a position conjugate with a pupil of the eye, a rotation unit arranged to rotate the light deflection member about a measurement optical axis of the measurement optical system, a memory arranged to store the ring fundus reflection image photo-received on the image-pickup element as a measurement image, an analysis unit connected with the memory which is arranged to perform analysis of the measurement image stored in the memory, and an output unit which is arranged to output a result of the analysis performed by the analysis unit, wherein the analysis unit detects the number of images or a width of an image in each of meridian directions in the measurement image and judges that the eye has irregular astigmatism when a portion in which the number of the images is two or a portion in which the width of the image goes beyond a predetermined level is detected.

Additional objects and advantages of the invention are set forth in the description which follows, are obvious from the description, or may be learned by practicing the invention. The objects and advantages of the invention may be realized and attained by the eye refractive power measurement apparatus in the claims.

BRIEF DESCRIPTION OF THE DRAWINGS

The accompanying drawings, which are incorporated in and constitute a part of this specification, illustrate an embodiment of the present invention and, together with the description, serve to explain the objects, advantages and principles of the invention. In the drawings.

DETAILED DESCRIPTION OF THE PREFERRED EMBODIMENTS

Figure 1:
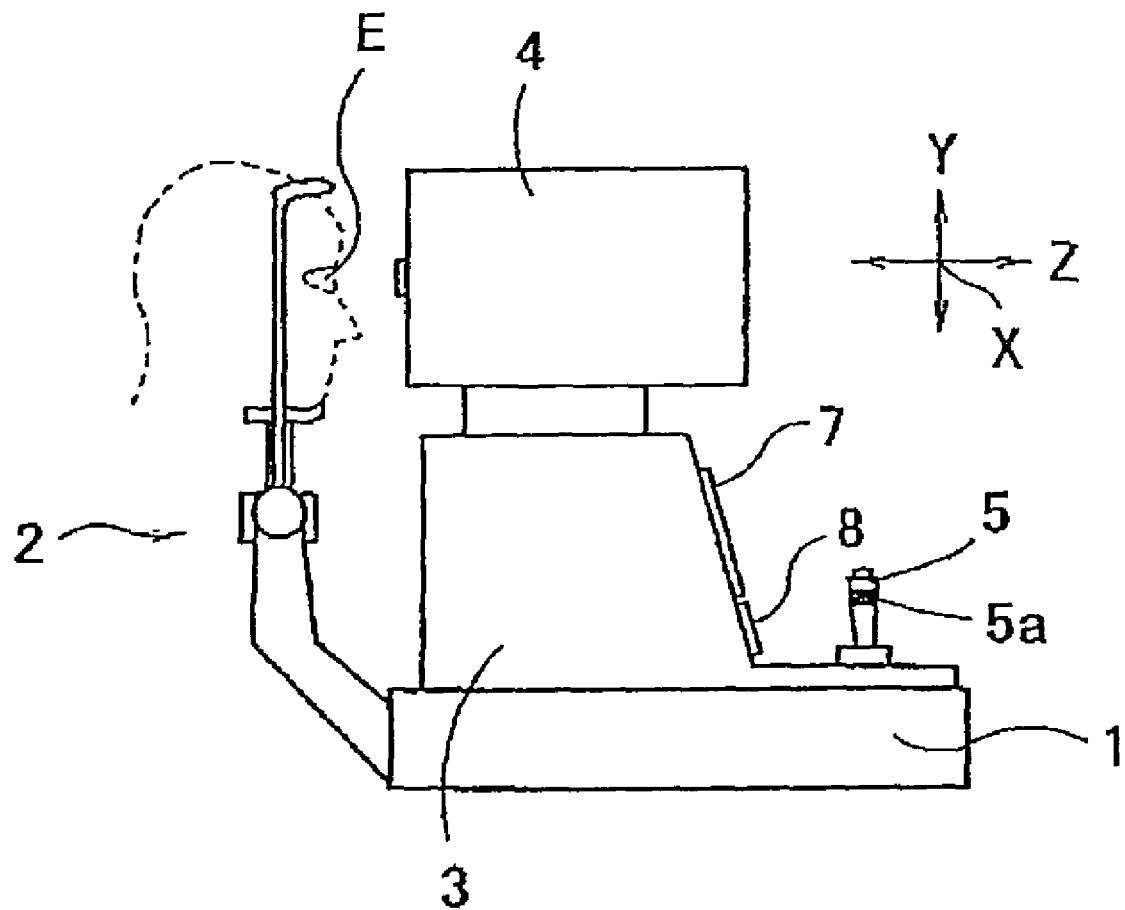
FIG. 1 is a schematic external view of an eye refractive power measurement apparatus according to a preferred embodiment of the present invention.

An eye refractive power measurement apparatus according to a preferred embodiment of the present invention is described below with reference to the accompanying drawings. FIG. 1 is a schematic external view of the eye refractive power measurement apparatus according to the preferred embodiment of the present invention. The measurement apparatus comprises a base 1, a face supporting unit 2 attached to the base 1, a mobile base 3 placed so as to be movable on the base 1, and a measurement unit 4 placed so as to be movable on the mobile base 3, which houses an optical system to be described later. The mobile base 3 is arranged to move in a right/left direction (an X-direction) and a back/forth direction (a Z-direction) on the base 1 through operation of a joystick 5. In addition, the measurement unit 4 is arranged to move in an up/down direction (a Y-direction) by a driving mechanism comprising a motor and other members through rotating operation of a rotation knob 5a. A monitor 7 for displaying various information such as an observation image and a measurement result of an examinee's eye E, and a switch unit 8 having switches for various settings are mounted on the mobile base 3.

Figure 2:
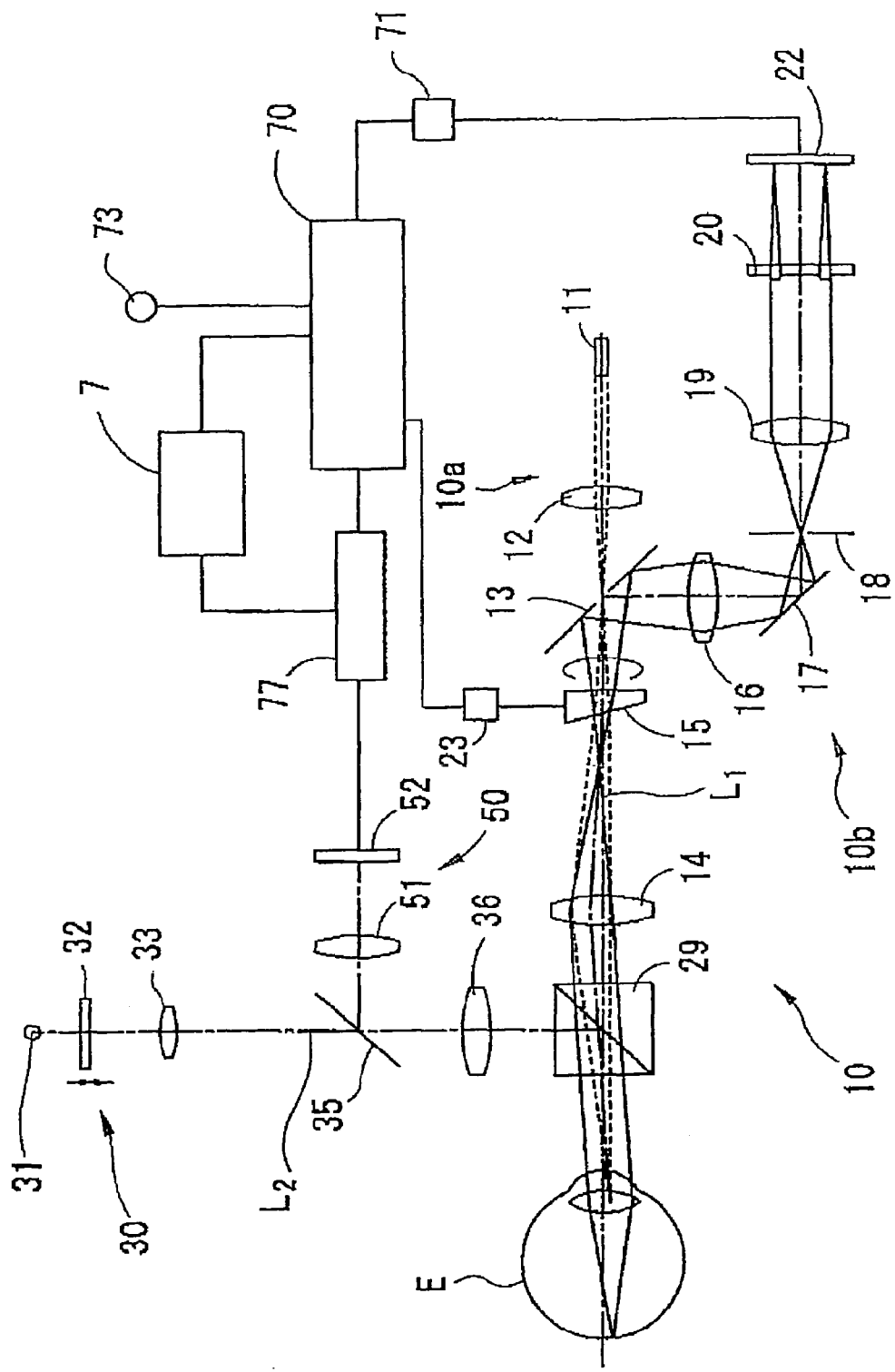
FIG. 2 is a view showing a schematic configuration of an optical system and a control system of the eye refractive power measurement apparatus.
Figure 3A:
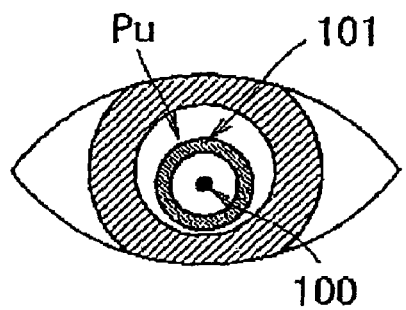
FIGS. 3A to 3D a reviews showing positional variations of photo-received light on a pupil of an examinee's eye.

FIG. 2 is a view showing a schematic configuration of the optical system and a control system of the eye refractive power measurement apparatus. A measurement optical system 10 comprises a projection optical system 10a for projecting spot-shaped light onto a fundus via a central pupillary portion of the examinee's eye E, and a photo-receiving optical system 10b for picking up fundus reflection light in a ring shape via a peripheral pupillary portion of the eye E. The projection optical system 10a comprises an infrared point light source 11 such as an LED and an SLD, a relay lens 12, a hole mirror 13, a prism 15 which is rotatably driven about a measurement optical axis L1 by a driving unit 23, and an objective lens 14 for measurement, which are placed in this order toward the eye E on the optical axis L1. The light source 11 is arranged to have a relationship conjugate with the fundus, and a hole portion of the hole mirror 13 is arranged to have a relationship conjugate with a pupil of the eye E. The prism 15 is placed at a position aside from a position conjugate with the pupil, and decenters light which passes therethrough from the optical axis L1. A beam splitter 29 that is an optical path bifurcating member is placed between the objective lens 14 for measurement and the eye E. The beam splitter 29 is arranged to reflect reflection light from an anterior-segment of the eye E toward an observation optical system 50, and to guide light from a fixation target optical system 30 to the eye E.

The photo-receiving optical system 10b shares the objective lens 14 for measurement, the prism 15 and the hole mirror 13 with the projection optical system 10a, and comprises a relay lens 16 and a mirror 17 which are placed on an optical path in a reflecting direction of the mirror 13, and a photo-receiving diaphragm 18, a collimator lens 19, a ring lens 20 and an image-pickup element 22 that is a two-dimensional photodetector such as a CCD which are placed on an optical path in a reflecting direction of the mirror 17. The photo-receiving diaphragm 18 and the image-pickup element 22 are arranged to have relationships conjugate with the fundus. An output of the image-pickup element 22 is connected to a control unit 70 via an image memory 71.

The ring lens 20 is placed at a position conjugate with the pupil in the photo-receiving optical system 10b, and is constituted of a lens portion where a cylindrical lens is formed in a ring shape on a flat plate, and a light shielding portion formed by coating for light shielding which is provided to portions on the flat plate other than the lens portion.

An objective lens 36 for observation, a half mirror 35, a projection lens 33, a fixation target 32 and a visible light source 31 are placed in this order on an optical axis L2 which is made coaxial with the optical axis L1 by the beam splitter 29. The light source 31 to the objective lens 36 for observation constitute the fixation target optical system 30. The light source 31 and the fixation target 32 are arranged to fog the eye E by moving in a direction of the optical axis L2. The light source 31 is arranged to illuminate the fixation target 32, and light from the fixation target 32 passes through the projection lens 33, the half mirror 35 and the objective lens 36. Then, the light is reflected by the beam splitter 29 and is guided to the eye E, and the eye E fixates the fixation target 32.

The observation optical system 50 comprises a photographing lens 51 and a CCD camera 52 that is an image-pickup element which are placed in a reflecting direction of the half mirror 35. An output of the camera 52 is connected to the monitor 7 via an image processing unit 77. An image of the anterior-segment of the eye E is formed on an image-pickup surface of the camera 52 through the beam splitter 29, the objective lens 36, the half mirror 35 and the photographing lens 51, and is displayed on the monitor 7 as an observation image.

Next, the operation of the apparatus having the above-described configuration will be described. At the time of measurement, an examiner observes the anterior-segment image displayed on the monitor 7 and a corneal reflection image by an alignment target projection optical system (not shown), and performs alignment of the measurement unit 4 with the eye E through the operation of the joystick 5 and the rotation knob 5a. When an alignment state of the measurement unit 4 becomes adequate, a measurement starting switch 73 is depressed and the measurement is initiated. The fixation target 32 by the fixation target optical system 30 is presented to the eye E, and the eye E is made to fixate it.

The control unit 70 controls the light source 11 to light up based on a measurement starting signal from the switch 73 and controls the driving unit 23 to rotate the prism 15 at high speed. Infrared light emitted from the light source 11 passes through the relay lens 12, the hole mirror 13, the prism 15, the objective lens 14 and the beam splitter 29, and forms a point-light-source image in a spot shape on the fundus. At this time, a projection image of the hole portion of the hole mirror 13 on the pupil (projection light on the pupil) is decentered and rotated at high speed by the prism 15 rotating about the optical axis L1.

Light of the point-light-source image projected onto the fundus is reflected and scattered and exits from the eye E, is collected by the objective lens 14, and is collected again at a position of the photo-receiving diaphragm 18 via the prism 15 rotating at high speed, the hole mirror 13, the relay lens 16 and the mirror 17. Then, an image is formed in a ring shape on the image-pickup element 22 by the use of the collimator lens 19 and the ring lens 20. At this time, the reflection light from the fundus passes through the prism 15 which is also used in the projection optical system 10a because the prism 15 is placed on an optical path shared between a projection optical path and a photo-receiving optical path, so that the reflection light is conversely scanned as if there were no decentering of the projection light and the reflection light (photo-received light) on the pupil in the subsequent optical systems.

In the measurement of the eye refractive power, preliminary measurement is performed first, and based on a result of the preliminary measurement, the light source 31 and the fixation target plate 32 are moved in the optical axis L2 direction, whereby the eye E is fogged. Then, main measurement is performed in a state where the eye E is fogged.

FIGS. 3A to 3D are views showing positional variations of the projection light and the photo-received light on the pupil. As shown, projection light 100 and photo-received light 101 on the pupil are decentered from and rotated about the center of a pupil Pu at which the measurement optical axis L1 is positioned while a mutual positional relationship is maintained therebetween. If the fundus reflection image on the image-pickup element 22 is captured with each passing moment, the fundus reflection image is made up of images which correspond to measurement positions at the passing moments. However, by rotating the prism 15 at high speed in a shorter cycle than a storage time of the image-pickup element 22, a ring-shaped image which are obtained by integrating the images can be detected from the image-pickup element 22 (see Japanese Patent Application Unexamined Publication No. 2005-185523 corresponding to U.S. Patent Publication No. 2005/0157261 by the same applicant).

An output signal from the image-pickup element 22 is stored in the image memory 71 as image data (a measurement image). Thereafter, based on the measurement image stored in the image memory 71, the control unit 70 specifies positions in meridian directions of the ring-shaped image. Based on the specified positions of the ring-shaped image, the control unit 70 performs ellipse fitting using a least-squares method or other method. Then, the control unit 70 obtains refractive errors in the meridian directions based on the shape of the obtained ellipse, and calculates values of the eye refractive power, and values of S (sphere power) C (cylinder power) and A (an astigmatic axial angle) of the eye E based on the refractive errors. A result of the measurement is displayed on the monitor 7.

Figure 4:
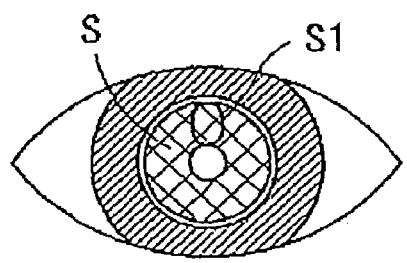
FIG. 4 is a view showing a measurement range on the pupil.
Figure 3B:
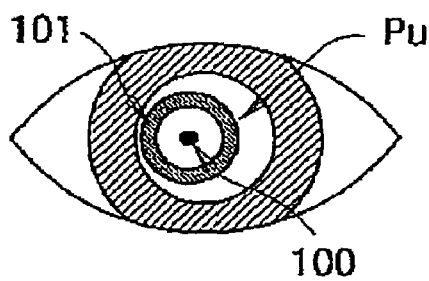
Figure 3C:
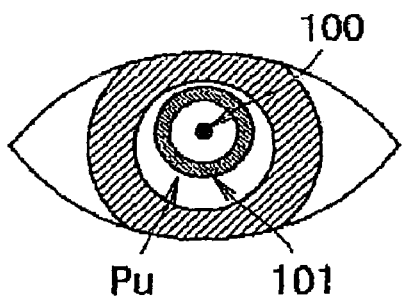
Figure 3D:
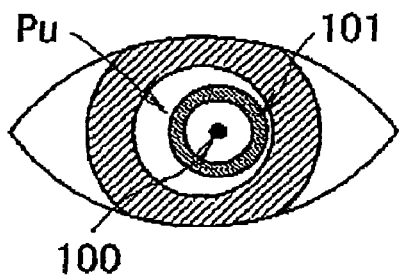

If the prism 15 placed at the position aside from the conjugate position with the pupil is rotated as described above at this time, the photo-received light to be picked up in a ring shape on the pupil is brought into a state of being decentered from and rotated about the pupillary center, whereby the measurement position on the pupil varies with time. Hence, a measurement range on the pupil in a case where the prism is rotated at high speed results in a range as shown in FIG. 4 (see the hatched area S). Therefore, a ring image which is to be obtained by being picked up by the image-pickup element 22 and being stored for the predetermined time is photo-received in the state of containing characteristics of the eye refractive power in a moving range of the ring-shaped image which is obtained by at least one rotation of the prism 15.

The ring image stored in the image memory 71 can be considered as data obtained by averaging the above-described characteristics of the refractive power of the cornea and the entire crystalline lens of the eye E in the moving range of the ring-shaped image. Further, information on the ring-shaped image in the meridian directions in the ring image can be considered as data obtained by averaging the characteristics of the refractive power in predetermined measurement regions formed by the varying measurement position. For example, the information on the ring-shaped image in the meridian direction of 90 degrees can be considered as the data obtained by averaging the characteristics of the refractive power in a measurement region S1 (see FIG. 4) on the pupil. Accordingly, in the obtained ring image, the information on the ring-shaped image such as a ring width, the number of rings and a luminance level varies partially (in the meridian directions) or entirely according to distribution of the refractive power.

Figure 5:
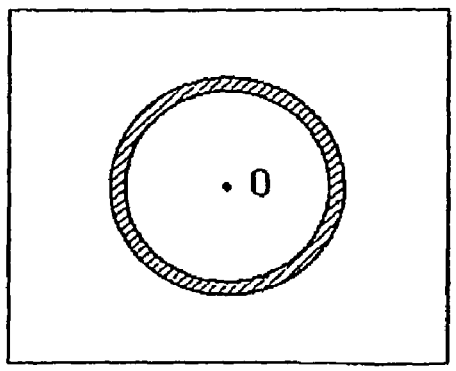
FIG. 5 is a view showing an example of a ring-shaped image to be obtained in a case where an examinee's eye is a normal eye.
Figure 6:
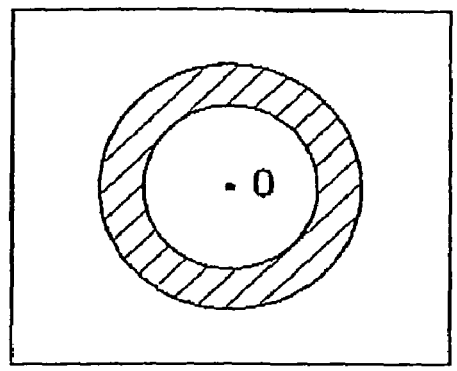
FIG. 6 is a view showing an example of a ring-shaped image to be obtained in a case where an examinee's eye has opacity in its optic media portion (the examinee has a cataract in his/her eye)

FIG. 5 to FIG. 8B are views showing examples of the ring-shaped images to be obtained on the photodetector in cases where examinees' eyes are in various conditions. FIG. 5 is a view showing an example of the ring-shaped image to be obtained in a case where an examinee's eye is a normal eye. FIG. 6 is a view showing an example of the ring-shaped image to be obtained in a case where an examinee's-eye has opacity in its optic media portion (where the examinee has a cataract in his/her eye).

Figure 7A:
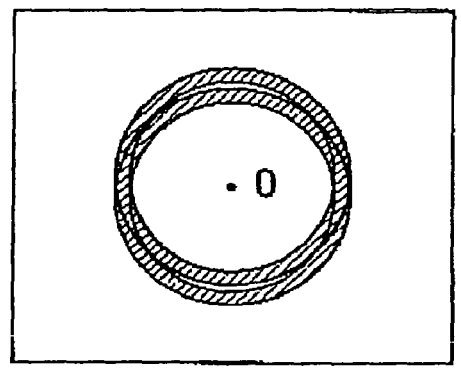
FIGS. 7A and 7B are views showing examples of a ring-shaped image to be obtained in a case where an examinee's eye has keratoconus, or suspected keratoconus.
Figure 7B:
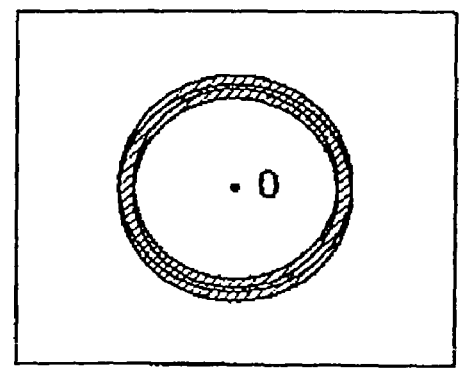
Figure 8A:
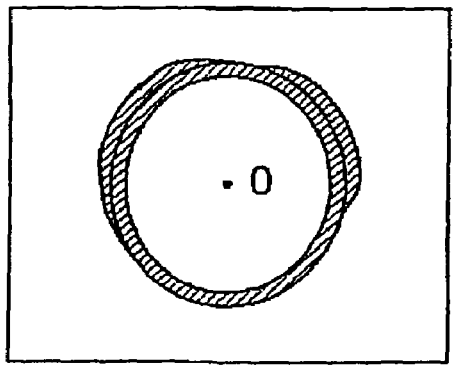
FIGS. 8A and 8B are views showing examples of a ring-shaped image to be obtained in a case where an examinee's eye has irregular astigmatism.
Figure 8B:
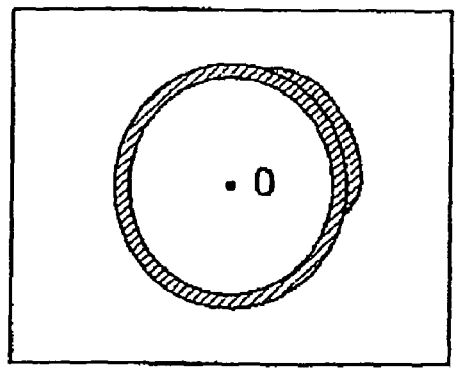

FIGS. 7A and 7B are views showing examples of the ring-shaped image to be obtained in a case where an examinee has keratoconus, or suspected keratoconus. FIGS. 8A and 8B are views showing examples of the ring-shaped image to be obtained in a case where an examinee's eye has irregular astigmatism.

In a ring image of a normal eye as shown in FIG. 5, the ring-shaped image is entirely bright (i.e., a peak value of a bright signal is large), and a ring width (a ring thickness) is small (sharp) around the entire ring-shaped image. In a ring image of a cataractous eye as shown in FIG. 6, the ring-shaped image is darker at least in halves thereof or in the whole (i.e., a peak value of a bright signal is small) and a ring width is larger compared with the ring image of a normal eye shown in FIG. 5 because the measurement light is scattered by the opaque portions.

In a ring image of an eye of an examinee who has keratoconus as shown in FIG. 7A, while entirely bright, the ring-shaped image includes portions in each of which two rings are picked up in regions in the ring image which are opposed to each other with respect to a center O of the measurement (indicating a center position to be used as a reference for obtaining the information on the ring-shaped image in the meridian directions, examples of which include an intersection point between the measurement optical axis L1 and an image-pickup surface of the image-pickup element 22, the center of the ring, and the barycenter of the ring). In a ring image of an eye of an examinee who has keratoconus as shown in FIG. 7B, while entirely bright, the ring-shaped image includes portions in each of which a ring width is larger in regions in the ring image which are opposed to each other with respect to the measurement center O. Besides, FIGS. 7A and 7B are the views showing the examples of the ring-shaped image in the case of keratoconus such that the corneal shape is roughly conic in an up-and-down direction taking a corneal center portion of the eye as the vertex of a corn while roughly spherical in a right-and-left direction. In this case, the ring-shaped image could include a portion in which two rings are picked up in one of regions in the ring image which are opposed to each other with respect to the measurement center O, and the ring-shaped image could include a portion in which a ring width is larger in the other region. If the corneal shape is roughly conic both in the up-and-down direction and the right-and-left direction taking the corneal center portion as the vertex of a corn, two rings could be picked up in all of the meridian directions.

In a ring image of irregular astigmatism (irregular astigmatism except for keratoconus) as shown in FIG. 8A, while entirely bright, the ring-shaped image includes portions in each of which a ring width is larger (or two rings are picked up) in regions in the ring image which are not opposed to each other with respect to the measurement center O. In a ring image of irregular astigmatism as shown in FIG. 8B, while entirely bright, the ring-shaped image includes a portion in which a ring width is larger (or two rings are picked up) in one region in the ring image.

Here, the information on the ring-shaped image in the meridian directions is studied based on the ring images shown in FIG. 5 to FIG. 8B, which shows that when one ring is picked up in each of the meridian directions and the ring width is small as in the case of a normal eye, the characteristics of the refractive power vary little even if the measurement position varies by the rotation of the prism 15. In addition, the study shows that when two rings are picked up in each of the meridian directions as in the case of severe keratoconus, there are portions where the characteristics of the refractive power vary abruptly in the meridian directions when the measurement position varies by the rotation of the prism 15. The study also shows that when the ring widths are larger in the meridian directions while the bright signals in the meridian directions of the ring-shaped image are strong as in the case of mild keratoconus, the characteristics of the refractive power vary gently in the meridian directions when the measurement position varies by the rotation of the prism 15.

Figure 9:
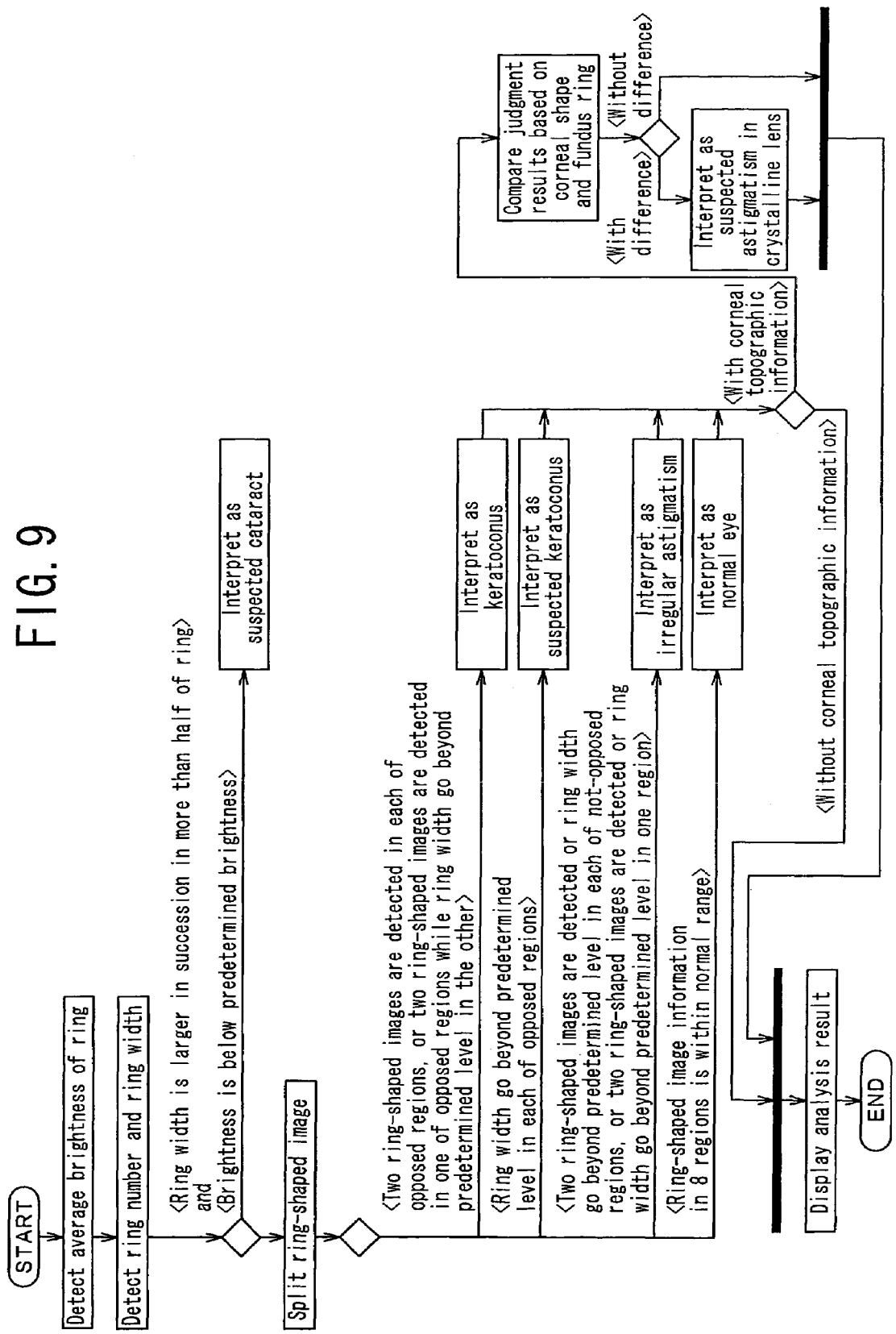
FIG. 9 is a flowchart for specifically illustrating a manner of obtaining information on a cornea and/or a crystalline lens of the eye other than refractive power.

Hereinafter, a specific example of a manner of obtaining information on the cornea and/or the crystalline lens of the examinee's eye E other than the refractive power (e.g., information on presence or absence of irregular astigmatism or keratoconus in the eye E) by analyzing the measurement image stored in the image memory 71 will be described referring to a flowchart of FIG. 9. First, a case of having no corneal topographic information will be described. The control unit 70 performs analysis of the eye E for keratoconus or irregular astigmatism based on the above-described ring image and the information on the ring-shaped image in the meridian directions in the ring image. More specifically, the control unit 70 detects a deviation of a photo-received position in each of the meridian directions of the ring-shaped image which is made because the refractive power varies with the measurement position when the measurement position on the pupil varies by the rotation of the prism 15, and judges whether or not each of the deviations of the photo-received positions satisfies a predetermined permissible range.

The control unit 70 detects peaks of the bright signals in the meridian directions of the ring-shaped image (portions where the bright signals take a downward turn from an upward turn) which is stored in the image memory 71, and detects values and the number of the peaks of the bright signals in the meridian directions. In addition, the control unit 70 detects the ring widths in the meridian directions of the ring-shaped image stored in the image memory 71. The ring widths can be detected, for example, from widths of half the values of the peaks of the bright signals in the meridian directions.

When the control unit 70 judges that an average value calculated from the peak values around the entire ring-shaped image is below a predetermined level (e.g., half of an average value calculated from the peak values in a normal eye) and that the detected ring widths in the meridian directions go beyond a predetermined level (e.g., a ring width three times as large as that in a normal eye) (i.e., the ring widths are larger) in succession in more than half of the ring-shaped image, the control unit 70 interprets the eye E as having a suspicion of cataract (as having opacity in its optic media portion), and controls the monitor 7 to display a result of the analysis. If two rings are detected, the control unit 70 detects ring widths thereof and makes the judgment on each of the ring widths.

Meanwhile, when judging that the above-described judgment conditions of cataract are not met, the control unit 70 shifts to the analysis (a judgment) of the eye E for keratoconus or irregular astigmatism. The control unit 70 splits the ring-shaped image every predetermined angle (e.g., splits it in eight at an angle of 45 degrees), and judges whether or not a portion in which the ring width goes beyond the predetermined width is detected and whether or not a portion in which the number of the rings is more than one is detected in each of split regions of the ring-shaped image. The judgment whether or not the portion in which the number of the rings is more than one is detected is made based on the number of the peaks of the bright signals in each of the meridian directions.

Figure 10:
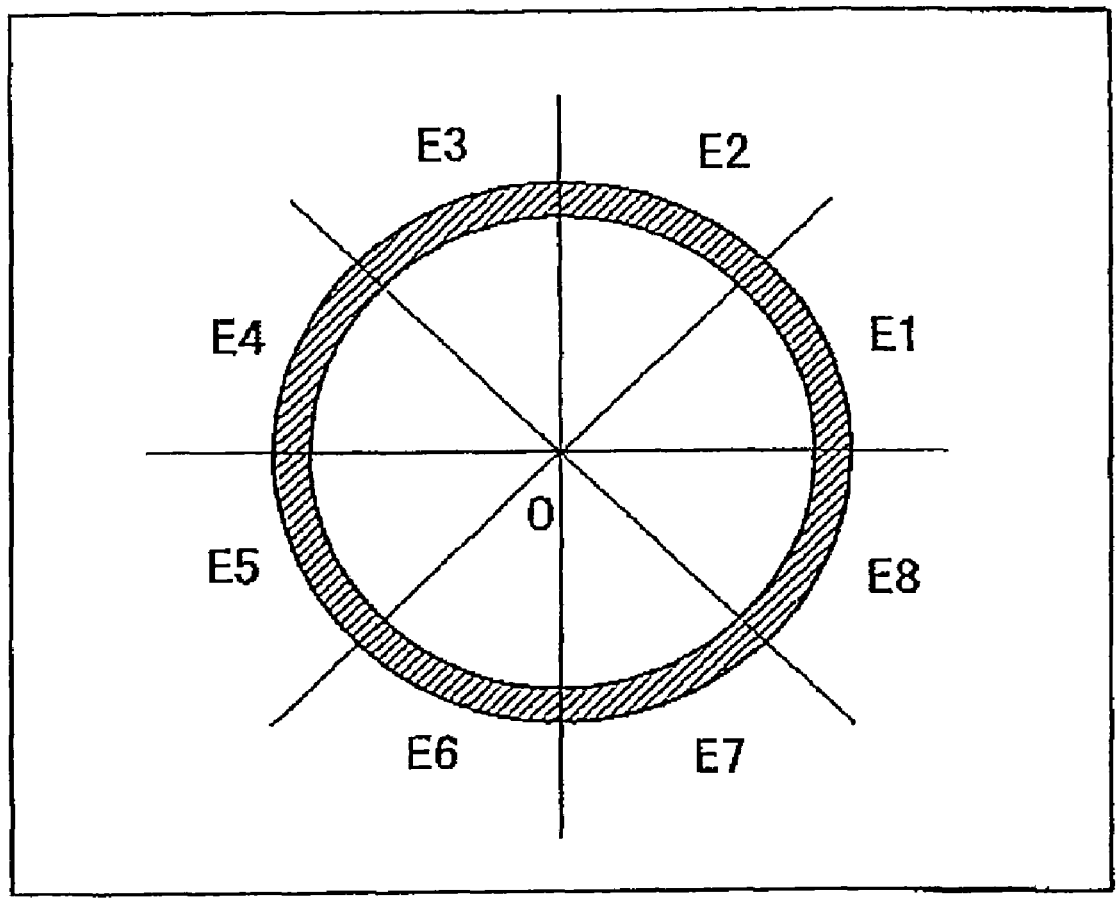
FIG. 10 is a view showing a ring-shaped image stored in a memory unit, which is divided into eighths.

To be more specific, the control unit 70 splits the ring-shaped image at intervals of 45 degrees with respect to the measurement center O as shown in FIG. 10. In this case, the ring-shaped image photo-received on the image-pickup element 22 is split in eight regions of a first ring region E1 to an eighth ring region E8 in order from zero degree at the intervals of 45 degrees. Accordingly, the information on the ring-shaped image (e.g., the ring width and the number of the rings) detected in the meridian directions can be split for the respective regions.

The control unit 70 judges the presence or absence of the portion in which the ring width goes beyond the predetermined width (e.g., a ring width two times larger than that in a normal eye) and the presence or absence of the portion in which the number of the rings is more than one with respect to each of the ring regions E1 to E8. When portions each of which includes two peaks are detected in the two ring regions which are opposed to each other with respect to the measurement center O (in the ring regions E1 and E5, the ring regions E2 and E6, the ring regions E3 and E7, or the ring regions E4 and E8), or when a portion which includes two peaks is detected in one of the opposed ring regions and a portion in which a ring width goes beyond the predetermined level is detected in the other ring region, the control unit 70 interprets the eye E as keratoconus and controls the monitor 7 to display as such. In addition, when portions each of which includes a ring width which goes beyond the predetermined level are detected in the ring regions which are opposed to each other with respect to the measurement center O, the control unit 70 interprets the eye E as suspected keratoconus and controls the monitor 7 to display as such.

When portions each of which includes two peaks or portions each of which includes a ring width which goes beyond the predetermined level are detected in the two ring regions which are not opposed to each other with respect to the measurement center O (e.g., the ring regions E2 and E4), or when a portion which includes two peaks is detected or a portion which includes a ring width which goes beyond the predetermined level is detected in one of the ring regions, the control unit 70 interprets the eye E as having irregular astigmatism and controls the monitor 7 to display as such.

When no portion which includes a ring width which goes beyond the predetermined level or no portion which includes two peaks is detected in each of the ring regions E1 to E8, in other words, when the information on the ring-shaped image in the ring regions is within a normal range, the control unit 70 interprets the eye E as a normal eye and controls the monitor 7 to display as such. Besides, strictly speaking, the characteristics of the refractive power vary even if the eye E is a normal eye when the measurement position varies by the rotation of the prism 15; however, the variances of the characteristics are narrow so as to fall within a range of 0.25 D or 0.5 D in terms of diopter, so that deviations of the photo-received positions in the meridian directions of the ring-shaped image are small.

In displaying the result of the analysis on the monitor 7 as described above, it is preferable to display it together with the values of the eye refractive power calculated based on the ring-shaped image stored in the image memory 71. In addition, in displaying the result of the analysis on the monitor 7, it is preferable that the control unit 70 controls the monitor 7 to display a message that the eye E has irregular astigmatism (including a message that the eye E has suspected irregular astigmatism) in a case where the eye E is interpreted as keratoconus or suspected keratoconus in the above-described analysis because keratoconus can be considered as a kind of irregular astigmatism.

The above-described configuration allows the apparatus to perform the analysis of the eye E for keratoconus or irregular astigmatism with accuracy in a wide range. It is also preferable that a measurement optical system is further provided to the apparatus, which projects a target for measuring the corneal shape of the eye E (e.g., a ring target) onto the cornea, and measures the corneal shape by picking up an image of the target projected onto the cornea. In this case, the control unit 70 performs the analysis of the eye E for keratoconus or irregular astigmatism based on the target image which is picked up. To be specific, the analysis of the eye E for keratoconus or irregular astigmatism is performed based on a standard deviation obtained from differences between refractive power of the cornea in the meridian directions which is obtained from the corneal shape measurement target image subjected to ellipse fitting, and refractive power in the meridian directions which is obtained from the actual target image.

Then, if a result of a judgment made based on the corneal shape measurement target image is that the eye E is a normal eye while a result of a judgment made based on the ring-shaped image for measuring the eye refractive power as described above is that the eye E has irregular astigmatism or the examinee has keratoconus, the control unit 70 makes a judgment of suspected astigmatism in the crystalline lens. In addition, if both the results of the judgments based on the corneal shape measurement target image and the ring-shaped image are that the eye E is abnormal, the control unit 70 interprets the cornea as having an abnormality and controls the monitor 7 to display a result of the analysis (see FIG. 9, charts downstream from <With corneal topographic information>)

In the above description, described is the measurement optical system for projecting the spot-shaped measurement light onto the fundus via the central pupillary portion, picking up the ring fundus reflection light via the peripheral pupillary portion, and photo-receiving the ring fundus reflection light on the two-dimensional image-pickup element, which is not limited thereto. For example, a measurement optical system can be also applied to the present invention, which comprises a projection optical system for projecting a ring-shaped image onto a fundus of an examinee's eye by projecting measurement light in a ring shape via a peripheral pupillary portion of the eye and a photo-receiving optical system for photo-receiving an image of the ring projected onto the fundus on a two-dimensional image-pickup element (see, Japanese Patent Application Unexamined Publication No. Hei01-129830), and in the measurement optical system, a light deflection member which deflects the measurement light so that the projection light in a ring shape is decentered and rotated on the pupil is provided on an optical path shared between the projection optical system and the photo-receiving optical system, and the light deflection member is rotatably driven.

In addition, the present invention is not limited to the measurement optical system in which the light passing through the peripheral pupillary portion is made to be the light in a ring shape. A measurement optical system can be also applied to the present invention, which is arranged so that eight spot images are photo-received on a two-dimensional image-pickup element by providing circular holes and small lenses in predetermined meridian directions (e.g., directions at intervals of 45 degrees) around the optical axis L1 as the center instead of providing the above-described ring lens 20. In other words, it is essential only that the measurement optical system be arranged so that the eye refractive power is measured by photo-receiving a pattern image having the shape of a predetermined pattern on the two-dimensional image-pickup element.

In the case of providing a light deflection member such as the prism 15 in a projection optical system and a photo-receiving optical system, the measurement optical system may be arranged so that the light deflection member is provided in each of the projection optical system 10*a* and the photo-receiving optical system 10*b*, and the light deflection members are rotated about the respective measurement optical axes in synchronization with each other. In this case, driving units arranged to respectively rotate the light deflection members are provided and are rotatably driven in synchronization with each other so that deflection directions of the light deflection members coincide with each other (see Japanese Patent Application Unexamined Publication No. 2005-185523 corresponding to U.S. Patent Publication No. 2005/0157261).

The foregoing description of the preferred embodiment of the invention has been presented for purposes of illustration and description. It is not intended to be exhaustive or to limit the invention to the precise form disclosed, and modifications and variations are possible in the light of the above teachings or may be acquired from practice of the invention. The embodiment chosen and described in order to explain the principles of the invention and its practical application to enable one skilled in the art to utilize the invention in various embodiments and with various modifications as is suited to the particular use contemplated. It is intended that the scope of the invention be defined by the claims appended hereto, and their equivalents.

What is claimed is:

1. An eye refractive power measurement apparatus comprising:
    a measurement optical system comprising
        a projection optical system for projecting measurement light onto a fundus of an examinee's eye, and
        a photo-receiving optical system having a two-dimensional image-pickup element, for photo-receiving the measurement light reflected from the fundus on the image-pickup element as one of a ring fundus reflection image and a substantially-ring fundus reflection image which is formed by a plurality of spot fundus reflection images;
    a light deflection member which is placed in the projection optical system and the photo-receiving optical system and is positioned aside from a position conjugate with a pupil of the eye;
    a rotation unit arranged to rotate the light deflection member about a measurement optical axis of the measurement optical system;
    a memory arranged to store the fundus reflection image photo-received on the image-pickup element as a measurement image;
    an analysis unit connected with the memory, which is arranged to perform analysis of the measurement image stored in the memory; and
    an output unit which is arranged to output a result of the analysis performed by the analysis unit,
    wherein the analysis unit detects one of the number of images and a width of an image in each of meridian directions in the measurement image, and judges that the eye has irregular astigmatism when one of a portion in which the number of the images is two and a portion in which the width of the image goes beyond a predetermined level is detected.

2. The eye refractive power measurement apparatus according to claim 1,
    wherein the analysis unit judges that the eye has keratoconus
    when one of portions in each of which the number of the images is two and portions in each of which the width of the image goes beyond the predetermined level is detected in regions in the measurement image which are opposed to each other with respect to a predetermined measurement center, or
    when a portion in which the number of the images is two is detected in one of the regions and a portion in which the width of the image goes beyond the predetermined level is detected in the other region.

3. The eye refractive power measurement apparatus according to claim 1, wherein the analysis unit judges that the eye has the irregular astigmatism when one of portions in each of which the number of the images is two and portions in each of which the width of the image goes beyond the predetermined level is detected in regions in the measurement image which are not opposed to each other with respect to a predetermined measurement center, or when one of a portion in which the number of the images is two and a portion in which the width of the image goes beyond the predetermined level is detected in one of the regions.

4. The eye refractive power measurement apparatus according to claim 1, wherein the analysis unit judges whether the eye has a cataract based on the measurement image stored in the memory, and judges whether the eye has the irregular astigmatism through screening by the cataract judgment.

5. The eye refractive power measurement apparatus according to claim 1, further comprising:

a projection optical system for projecting a target for measuring a corneal shape onto a cornea of the eye; and an image-pickup optical system for picking up an image of the target projected onto the cornea, wherein the analysis unit performs analysis of the target image obtained by the image-pickup optical system and judges whether or not the eye has the irregular astigmatism, and judges that the eye has suspected astigmatism in a crystalline lens when the eye is judged as a normal eye based on a result of the analysis of the target image while the eye is judged as having the irregular astigmatism based on a result of the analysis of the measurement image.

6. The eye refractive power measurement apparatus according to claim 1, wherein the light deflection member is placed on an optical path shared between the projection optical system and the photo-receiving optical system.

7. The eye refractive power measurement apparatus according to claim 1, wherein the light deflection member is placed in each of the projection optical system and the photo-receiving optical system, and the rotation unit rotates the light deflection members about respective measurement optical axes of the projection optical system and the photo-receiving optical system in synchronization with each other.

* * * * *